| United States Patent [19] | [11] | 4,410,353 |
|---|---|---|
| Theissen | [45] | Oct. 18, 1983 |

[54] HERBICIDAL N-SULFONYL 5-[SUBSTITUTED PHENOXY]-2-SUBSTITUTED BENZAMIDES

[75] Inventor: Robert J. Theissen, Bridgewater, N.J.

[73] Assignee: Rhone-Poulenc Agrochimie, Lyons, France

[21] Appl. No.: 284,304

[22] Filed: Jul. 17, 1981

[51] Int. Cl.$^3$ .................................... C07D 275/06
[52] U.S. Cl. ................................. 71/91; 71/124; 548/210
[58] Field of Search ............... 548/210; 71/90, 124, 71/91

[56] References Cited

U.S. PATENT DOCUMENTS

| 2,949,399 | 8/1960 | Lo | 548/210 |
| 3,784,635 | 1/1974 | Theissen | 560/21 |
| 4,006,007 | 4/1977 | Bollinger et al. | 71/76 |
| 4,063,929 | 12/1977 | Bayer et al. | 71/115 |
| 4,209,318 | 6/1980 | Johnson | 198/732 |
| 4,285,723 | 8/1981 | Cartwright et al. | 71/103 |

FOREIGN PATENT DOCUMENTS

| 13660 | 7/1980 | European Pat. Off. . |
| 20052 | 12/1980 | European Pat. Off. . |
| 30676 | 6/1981 | European Pat. Off. . |
| 48-35457 | of 1973 | Japan | 548/210 |
| 48-05907 | of 1973 | Japan | 71/91 |
| 54-35217 | of 1979 | Japan | 71/91 |

*Primary Examiner*—Donald G. Daus
*Assistant Examiner*—G. Hendricks
*Attorney, Agent, or Firm*—Morgan, Finnegan, Pine, Foley & Lee

[57] ABSTRACT

There are provided herbicidal N-sulfonyl 5-[substituted phenoxy or pyridyloxy]-2-substituted benzamides.

3 Claims, No Drawings

HERBICIDAL N-SULFONYL 5-[SUBSTITUTED PHENOXY]-2-SUBSTITUTED BENZAMIDES

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. patents which describe such compounds and the like include U.S. Pat. Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

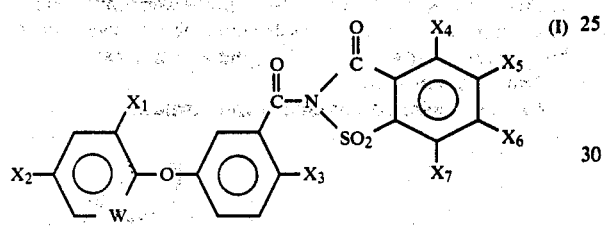

where:

(i) W is C-$X_8$ or N; and (ii) $X_1$, $X_2$, $X_3$, $X_4$, $X_5$, $X_6$, $X_7$ and $X_8$ are groups which are capable of being incorporated into formula I and which collectively impart herbicidal activity thereto. Preferably, $X_8$ is halogen (e.g., F, Br or, especially, Cl) or, especially, H. Examples of the groups $X_1$, $X_2$ and $X_3$ include halogen (e.g., F, Cl and Br), polyhaloalkyl (e.g., $C_1$-$C_4$ alkyl with from 2-9 halogens such as, especially, $CF_3$), $NO_2$, CN, alkyl (e.g., $C_1$-$C_4$ alkyl), $SO_2$ alkyl (e.g., having 1-4 carbon atoms), $SO_2NH_2$, NO, COO alkyl (e.g., having 2-5 carbon atoms) and COOH.

Examples of the groups $X_4$, $X_5$, $X_6$ and $X_7$ include those examples mentioned hereinabove with respect to $X_1$, $X_2$, and $X_3$.

A preferred form of Formula I is represented by the formula:

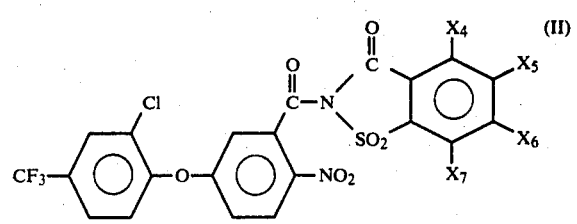

A preferred compound according to Formula I is:

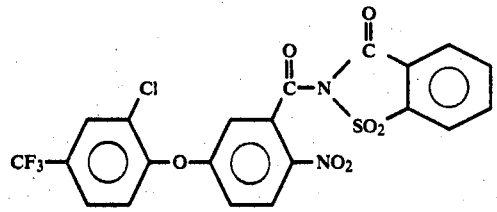

The following compound as defined by formula I was prepared:

| Compound No. | Structure | m.p. °C. |
|---|---|---|
| 1 | ![structure] | 179–80° |

EXAMPLE

Preparation of Compound 1

To a stirred solution of Saccharin (183 g, 1.0 mole) and triethylamine (110 g, 1.1 mole) in acetone (2500 ml) was added 5-[2-chloro-4-(trifluoromethyl)phenoxy]-2-nitrobenzoyl chloride (380 g, 1.0 mole) in acetone (500 ml) over 10 minutes. The reaction was heated to reflux for 6 hours and then allowed to cool to room temperature. The solution was further cooled to $-5°$ C. and the white precipitate filtered off. The acetone filtrate was concentrated to give a crude solid which was triturated with methanol and dried to give 422 g of white solid, m.p. 179°–80° C.

I.R. (nujol mull): C=O 1765 and 1715 $cm^{-1}$.

Herbicidal Effectiveness

Method of Propagating Test Species

Crop and weed species are planted in 8"×10" disposable fiber flats containing potting soil to provide each flat with a 4" row of all test species. Crop species consist of field corn (CN), cotton (CT), and soybeans (SB). The weed species consist of foxtail millet (FM), green foxtail (GF), velvetleaf (VL), cocklebur (CB), wild mustard (WM) and pigweed (PW). Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3–4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. A 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1 percent.

Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0-100 percent injury and control scale. Special physiological effects are rated as to intensity also at this time.

The herbicidal test data is reported for certain compounds of the present invention. The following lists metric equivalents for rates expressed in terms of lbs./acre.

| Application Rate | |
|---|---|
| US -lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |
| 0.125 | 0.14 |
| 0.0625 | 0.07 |

Test results are set forth in Table I pre-emergence and post-emergence.

TABLE I

| Compound No. | Dosage Lbs./Acre | Pre-Emergence | | | | | | | | | Post-Emergence | | | | | | | | |
|---|---|---|---|---|---|---|---|---|---|---|---|---|---|---|---|---|---|---|---|
| | | FM | GF | VL | CB | WM | PW | CT | CN | SB | FM | GF | VL | CB | WM | PW | CT | CN | SB |
| 1 | 2 | 30 | 50 | 40 | 0 | 90 | 90 | 10 | 0 | — | 90 | 80 | 70 | 60 | 100 | 100 | 50 | 50 | 30 |
| | 1 | 30 | 40 | 20 | 40 | 90 | 80 | 0 | 20 | — | 80 | 80 | 70 | 60 | 100 | 100 | 40 | 30 | 60 |
| | ½ | 0 | 0 | 20 | 0 | 90 | 80 | 0 | 20 | — | 70 | 60 | 50 | 60 | 90 | 100 | 40 | 30 | 60 |
| | ¼ | 0 | 0 | 20 | 60 | 80 | 30 | 20 | 10 | — | 70 | 30 | 20 | 60 | 80 | 100 | 30 | 20 | 30 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

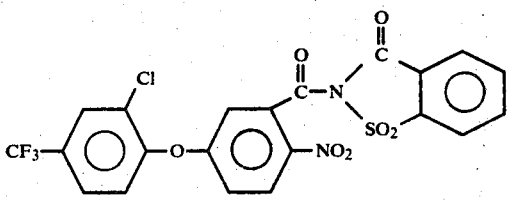

2. A herbicidal composition comprising a herbicidally effective amount of a compound according to claim 1 and an agronomically acceptable carrier.

3. A method of killing weeds in a crop field containing the same which comprises contacting said weeds with a herbicidally effective amount of a compound according to claim 1.

* * * * *